(12) United States Patent
Yi et al.

(10) Patent No.: US 11,540,704 B2
(45) Date of Patent: Jan. 3, 2023

(54) FLEXIBLE MECHANISM

(71) Applicant: INDUSTRY-UNIVERSITY COOPERATION FOUNDATION HANYANG UNIVERSITY ERICA CAMPUS, Ansan-si (KR)

(72) Inventors: Byung-Ju Yi, Bucheon-si (KR); Semin Oh, Anyang-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 350 days.

(21) Appl. No.: 16/562,839

(22) Filed: Sep. 6, 2019

(65) Prior Publication Data

US 2019/0387959 A1    Dec. 26, 2019

Related U.S. Application Data

(63) Continuation of application No. PCT/KR2018/002629, filed on Mar. 6, 2018.

(30) Foreign Application Priority Data

Mar. 6, 2017  (KR) .......................... 10-2017-0028267

(51) Int. Cl.
*A61B 1/005* (2006.01)
*A61B 1/00* (2006.01)
(Continued)

(52) U.S. Cl.
CPC ............ *A61B 1/0057* (2013.01); *A61B 1/005* (2013.01); *A61B 1/0055* (2013.01);
(Continued)

(58) Field of Classification Search
CPC .............. A61B 17/29; A61B 2017/003; A61B 2017/2901; A61B 1/0057; A61B 1/00073;
(Continued)

(56) References Cited

U.S. PATENT DOCUMENTS 3,071,161 A * 1/1963 Ulrich ...................... B25J 18/06
138/120
2007/0112355 A1    5/2007 Salahieh et al.
(Continued)

FOREIGN PATENT DOCUMENTS

CN        105828738 A     8/2016
JP        2007-301285 A   11/2007
(Continued)

OTHER PUBLICATIONS

International Search Report of PCT/KR2018/002629 dated May 3, 2018 [PCT/ISA/210].
(Continued)

*Primary Examiner* — Brooke Labranche
(74) *Attorney, Agent, or Firm* — Sughrue Mion, PLLC

(57) ABSTRACT

Provided is a flexible mechanism. The flexible mechanism comprises: a flexible backbone which is introduced into a treatment area in the human body and which bends along a path in the human body; and a wire for transmitting an operation force provided through a handler prepared at one end of the flexible backbone to an end-effector prepared at the other end of the flexible backbone, wherein the wire
(Continued)

extends from the one end of the flexible backbone to the other end of the flexible backbone and can wind around the outer circumferential surface of the flexible backbone in multiples of 360 degrees or passes through a spiral path formed on an inner surface in multiples of 360 degrees.

5 Claims, 9 Drawing Sheets
(3 of 9 Drawing Sheet(s) Filed in Color)

(51) Int. Cl.
| | | |
|---|---|---|
| *A61B 1/01* | (2006.01) | |
| *A61B 1/018* | (2006.01) | |
| *A61B 1/267* | (2006.01) | |
| *A61B 1/273* | (2006.01) | |
| *A61B 1/31* | (2006.01) | |
| *A61B 17/00* | (2006.01) | |
| *A61B 17/29* | (2006.01) | |
| *A61B 34/00* | (2016.01) | |

(52) U.S. Cl.
CPC ............ *A61B 1/00073* (2013.01); *A61B 1/01* (2013.01); *A61B 1/018* (2013.01); *A61B 1/2676* (2013.01); *A61B 1/2736* (2013.01); *A61B 1/31* (2013.01); *A61B 17/29* (2013.01); *A61B 2017/003* (2013.01); *A61B 2017/2902* (2013.01); *A61B 2034/715* (2016.02)

(58) Field of Classification Search
CPC ......... A61B 1/005; A61B 1/0055; A61B 1/01; A61B 1/018; A61B 1/2676; A61B 1/2736; A61B 1/31
See application file for complete search history.

(56) References Cited

U.S. PATENT DOCUMENTS

| | | | |
|---|---|---|---|
| 2009/0099420 A1* | 4/2009 | Woodley | ............. A61B 1/0053 600/142 |
| 2011/0196419 A1 | 8/2011 | Cooper | |
| 2013/0190649 A1 | 7/2013 | Lee | |
| 2016/0001038 A1 | 1/2016 | Romo et al. | |

FOREIGN PATENT DOCUMENTS

| | | |
|---|---|---|
| JP | 2009-142513 A | 7/2009 |
| JP | 2012-200518 A | 10/2012 |
| KR | 10-0921539 B1 | 10/2009 |
| KR | 10-0921656 B1 | 10/2009 |
| KR | 10-1258779 B1 | 4/2013 |
| WO | 94/14494 A2 | 7/1994 |
| WO | 94/14494 A3 | 7/1994 |
| WO | 2015/061756 A1 | 4/2015 |
| WO | 2015/093602 A1 | 6/2015 |
| WO | 2017/013942 A1 | 1/2017 |

OTHER PUBLICATIONS

Extended European Search Report dated Dec. 10, 2020 from the European Patent Office in EP Application No. 18763195.7.

* cited by examiner

FLEXIBLE MECHANISM

BACKGROUND OF THE INVENTION

1. Field of the Invention

The present invention relates to a flexible mechanism, and more particularly to a mechanism in which a plurality of wires that operate an end effector is wound on the outer circumferential surface of a flexible backbone in a multiple of 360 degrees or at an angle of 360 degrees or more, or a flexible mechanism that passes through a spiral passage on the inner surface of the flexible backbone at an angle of a multiple of 360 degrees.

2. Description of the Prior Art

A flexible mechanism is used for the purpose of observing or treating a narrow space having curves. The flexible mechanism is used for an esophagogastroduodenoscope, a colonoscope, or a bronchoscope, and includes a flexible tube, a steering device and a tool connected to one end of the flexible tube, a steering operating mechanism (for example, a handle or a button) connected to an opposite end of the flexible tube, and a flexible tube wire that delivers an operation force of the steering operation mechanism to the steering device.

A conventional flexible mechanism is provided with a plurality of wires extending in the lengthwise direction of a flexible tube in a linear form. When the flexible tube is introduced into a curved space, the flexible tube is deflected, and the wire in the interior of the flexible tube is also deflected. Accordingly, a separate wire control algorithm or mechanical device is required to compensate for the deflection of the wire due to the deflection of the flexible tube, and the operation control of the flexible mechanism may not be easy.

Accordingly, development of a flexible mechanism that is not influenced by the deflection of the flexible tube occurring when the flexible tube is introduced into the curved space has been required, and the present inventors invented a flexible mechanism that is not influenced by deflection of a flexible tube.

SUMMARY OF THE INVENTION

A technical purpose of the present invention is to provide a flexible mechanism which accurately delivers an operation force of a handler to an end effector.

Another technical purpose of the present invention is to provide a flexible mechanism which makes the length of a flexible backbone and the length of a path of a wire the same even when the flexible backbone is deflected.

The objectives of the present invention are not limited to the above-described ones.

In order to solve the technical objects, the present invention provides a flexible mechanism.

In accordance with an aspect of the present invention, a flexible mechanism includes a flexible backbone introduced into a medical operation part in a human body and deflected along a path in the human body, and a wire configured to deliver an operation force provided through a handler provided at one end of the flexible backbone to an end effector provided on an opposite side of the flexible backbone, wherein the wire extends from one end to an opposite end of the flexible backbone, and is wound on the outer circumferential surface or the inner circumferential surface of the flexible backbone by a multiple of 360 degrees.

According to an embodiment, the length of an area of the wire, which protrudes to opposite ends of the flexible backbone, may be constant even when the flexible backbone is deflected.

According to an embodiment, the wire may be wound the outer circumferential surface of the flexible backbone in a multiple of 360 degrees in a spiral shape.

According to an embodiment, the multiple may be a positive integer of 1 or more.

According to an embodiment, the flexible mechanism may further include a wire protection part wound on the outer circumferential surface of the flexible backbone from one end to an opposite end of the flexible backbone in a multiple of 360 degrees and provided with a movement path for the wire.

According to an embodiment, the wire may be provided along the movement path of the wire protection part.

According to an embodiment, the wire protection part is bonded to the flexible backbone.

According to an embodiment, a groove wound on the outer circumferential surface of the flexible backbone from one end to an opposite end of the flexible backbone in a multiple of 360 degrees may be formed on the outer circumferential surface of the flexible backbone, and the wire protection part may be seated in the groove.

According to an embodiment, the flexible backbone may further include a spiral wire passage recessed from a surface of the flexible backbone, and the wire may pass along the spiral wire passage from one end to an opposite end of the flexible back bone in a multiple of 360 degrees.

In accordance with an aspect of the present invention, a flexible mechanism includes a flexible backbone introduced into a medical operation part in a human body and deflected along a path in the human body, and at least two wires configured to deliver an operation force provided through a handler provided at one end of the flexible backbone to an end effector provided on an opposite side of the flexible backbone, and wound on the outer circumferential surface or the inner circumferential surface of the flexible backbone in a multiple of 360 degrees, wherein the lengths of the at least two wires between the opposite ends of the flexible backbone are the same when the flexible backbone is linear and the flexible backbone is deflected.

According to an embodiment, the flexible mechanism may further include at least two wire protection parts wound on the outer circumferential surface of the flexible backbone from one end to an opposite end of the flexible backbone in a multiple of 360 degrees and provided with at least two movement paths for the wires.

According to an embodiment, the at least two wire protection parts may be bonded to the flexible backbone, and the at least two wire protection parts may be bonded to each other.

According to an embodiment, at least two grooves wound on the outer circumferential surface of the flexible backbone from one end to an opposite end of the flexible backbone in a multiple of 360 degrees may be formed on the outer circumferential surface of the flexible backbone, and the wire protection parts may be seated in the grooves.

In accordance with an aspect of the present invention, a flexible mechanism includes a tube provided with a wire in the interior thereof, and a backbone provided in the lengthwise direction of the tube, wherein a structure in which the tube is wound about the central axis of the backbone in a multiple of 360 degrees.

The wire of the flexible mechanism according to the embodiment of the present invention is wound on the flexible backbone in a multiple of 360 degrees to make the length of the flexible backbone and the length of the path of the wire the same even when the flexible backbone is deflected, and to precisely deliver the operation force provided by the handler to the end effector.

Further, the groove is formed in the flexible backbone of the flexible mechanism according to the embodiment of the present invention to make it easy to adhere and wind the wire on the flexible backbone.

BRIEF DESCRIPTION OF THE DRAWINGS

The application file contains at least one drawing executed in color. Copies of this application publication with the color drawings will be provided by the Office upon request and payment of the necessary fee.

The above and other objects, features, and advantages of the present invention will be more apparent from the following detailed description taken in conjunction with the accompanying drawings, in which.

DETAILED DESCRIPTION OF THE EXEMPLARY EMBODIMENTS

Figure 1:
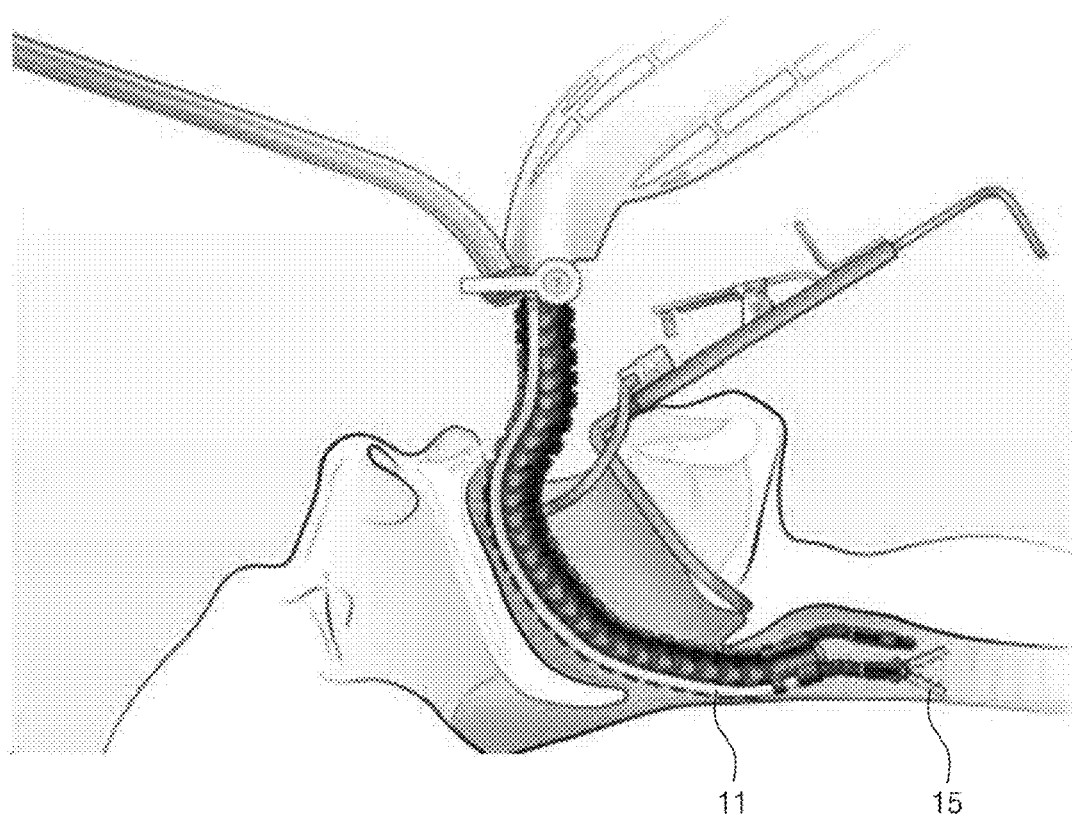
FIG. 1 is a view illustrating an usage example of a general flexible mechanism.

Hereinafter, preferred embodiments of the present invention will be described in detail with reference to the accompanying drawings. However, the technical spirit of the present invention is not limited to the embodiments, but may be realized in different forms. The embodiments introduced here are provided to sufficiently deliver the spirit of the present invention to those skilled in the art so that the disclosed contents may become thorough and complete.

When it is mentioned in the specification that one element is on another element, it means that the first element may be directly formed on the second element or a third element may be interposed between the first element and the second element. Further, in the drawings, the thicknesses of the membrane and areas are exaggerated for efficient description of the technical contents.

Further, in the various embodiments of the present invention, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. Further, the terms "including" and "having" are used to designate that the features, the numbers, the steps, the elements, or combination thereof described in the specification are present, and may be understood that one or more other features, numbers, step, elements, or combinations thereof may be added.

Further, in the specification, the expression 'a constant length' or 'the same length' may be understood as meaning 'a substantially constant length' or 'substantially the same length'.

Further, in the following description of the present invention, a detailed description of known functions and configurations incorporated herein will be omitted when it may make the subject matter of the present invention unnecessarily unclear.

Figure 2A:
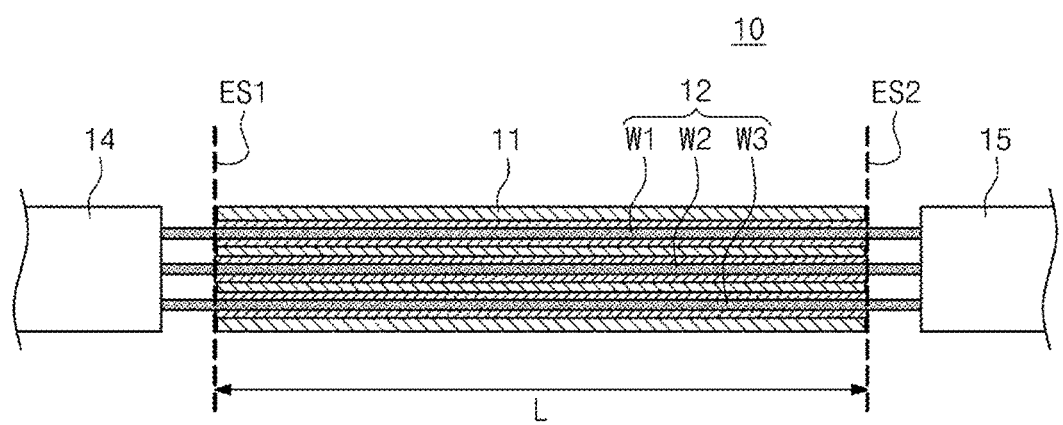
FIGS. 2A and 2B are views illustrating a general flexible mechanism.
Figure 2B:
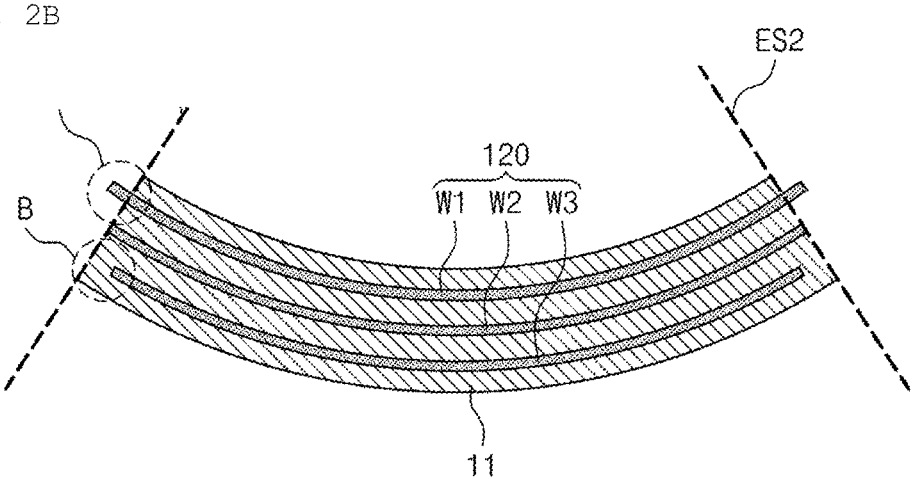

FIG. 1 is a view illustrating an usage example of a general flexible mechanism. FIGS. 2A and 2B is a view illustrating a general flexible mechanism.

Referring to FIG. 1, the general flexible mechanism may be applied to a curved surgery system for surgery of a throat. The flexible mechanism may include a flexible backbone 11, a handler (not illustrated), and an end effector 15. The flexible backbone 11 includes a wire in the interior thereof, and may be introduced into a human body. The handler is connected to one end of the flexible backbone 11, and may drive the flexible mechanism by operating the end effector 15 through the wire. The end effector 15 is connected to an opposite end of the flexible backbone 11 and is introduced into the human body, and may be operated by the handler to perform a throat surgery. A problem of the general flexible mechanism described with reference to FIG. 1 will be described with reference to FIGS. 2A and 2B.

Referring to FIG. 2A, the general flexible mechanism 10 may include a flexible backbone 11, a wire 12, a handler 14, and an end effector 15.

The flexible backbone 11 is introduced into a human body and is deflected along a path of the human body, and includes a wire 12 in the interior thereof. One end of the flexible backbone 11, which is not introduced into the human body, may be connected to the handler 14, and an opposite end of the flexible backbone 11, which is introduced into the human body, may be connected to the end effector 15.

The wire 12 is provided in the interior of the flexible backbone 11, and an operation force provided by the handler 14 is delivered to the end effector 15. Two or more wires 12 may be provided. The two or more wires W1, W2, and W3 may be provided to extend in a direction that is the same as the lengthwise direction of the flexible backbone 11.

The handler 14 is disposed outside the human body, and provides an operation force to the wires 12 according to an operation of a medical operator to adjust the angle or operation of the end effector 15.

The end effector 15 may directly connect a target portion, and may perform a specific action according to the operation force provided by the handler 14. For example, the end effector 15 may be provided in the form of a nipper.

Referring to FIG. 2B, it can be seen that when the flexible mechanism 10 in a linear form is deflected, the lengths of the wires W1, W2, and W3 in the interior of the flexible backbone 11 vary. That is, relative displacements occur between the flexible backbone 11 and the wires W1, W2, and W3.

For a more detailed description, referring to FIG. 2A again, when the flexible backbone 11 has a linear form, a distance between a first cross-section ES1 and a second cross-section ES2 of the flexible backbone 11 may be L. In this case, distances between the first cross-sections ES1 and the second cross-sections ES2 of the wires W1, W2, and W3 provided in the interior of the flexible backbone 11 may be the same as L. In this case, because the lengths of the flexible backbone 11 and the wires W1, W2, and W2 are the same, it may be understood that the relative displacements are 0.

Then, as illustrated in FIG. 2B, when the flexible mechanism 10 is deflected, the distance between the first cross-section ES1 and the second cross-section ES2 of the flexible backbone 11 may become longer or shorter than that of an initial state L. For example, referring to area A illustrated in FIG. 2B, in an area located on the inner side with respect to the deflection direction of the flexible backbone 11, the distance between the first cross-section ES1 and the second cross-section ES1 may become shorter than the initial state L. Accordingly, the first wire W1 protrudes while passing by the first cross-section ES1 and the second cross-section ES2. In this case, because the protruding first wire W1 operates the end effector 15 in an unintended direction or an unintended force, a danger may be caused in a medical operation or a surgery. As another, referring to area B illustrated in FIG. 2B, in an area located on the outer side with respect to the deflection direction of the flexible backbone 11, the distance between the first cross-section ES1 and the second cross-section ES1 may become longer than the initial state L. Accordingly, the third wire W3 does not arrive between the first cross-section ES1 and the second cross-section ES2. Even in this case, because the third wire W3 inserted into the flexible backbone 11 operates the end effector 15 in an unintended direction or an unintended force, a danger may be caused in a medical operation or a surgery.

Figure 3:
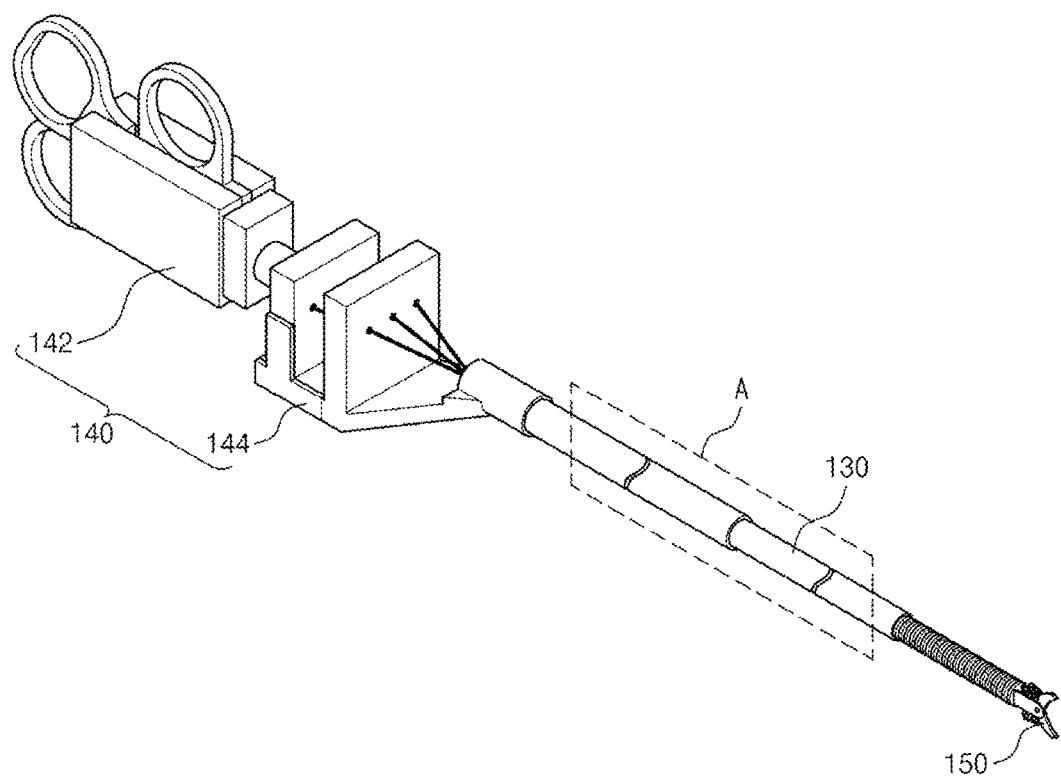
FIG. 3 is a perspective view of a flexible mechanism according to an embodiment of the present invention.
Figure 4:
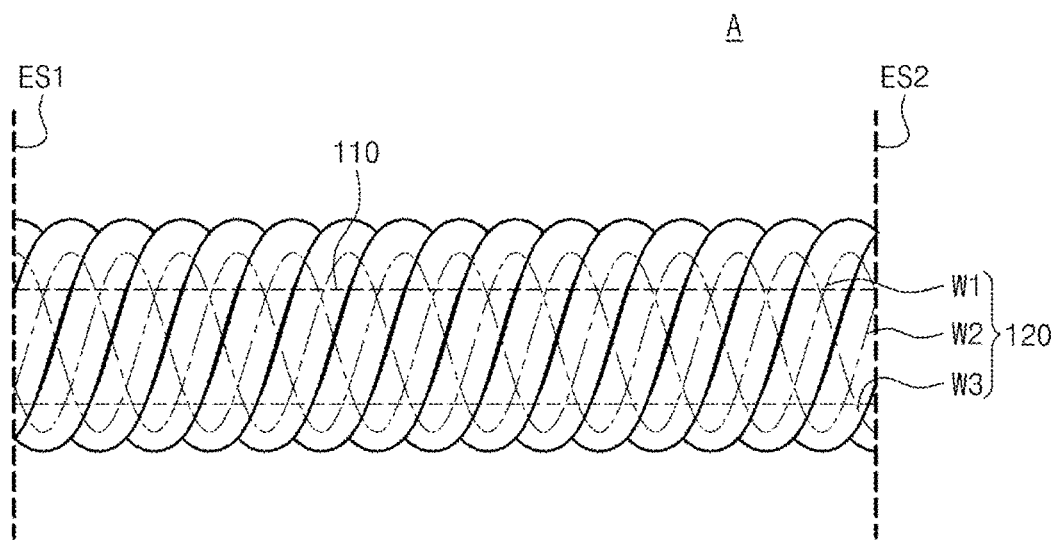
FIG. 4 is a view illustrating A of FIG. 3.

FIG. 3 is a perspective view of a flexible mechanism according to an embodiment of the present invention. FIG. 4 is a view illustrating A of FIG. 3.

Referring to FIGS. 3 and 4, the flexible mechanism 100 according to the embodiment may include a flexible backbone 110, a wire 120, and a wire protection part 130. Moreover, the flexible mechanism may further include a handler 140 and an end effector 150.

The flexible mechanism 100 according to the embodiment of the present invention may be used as a tool for diagnosis or treatment, such as an endoscope for a human body or an industrial endoscope including an esophagogastroduodenoscope, a colonoscope, a bronchoscope, which is inserted into a human body.

The flexible backbone 110 is introduced into a human body and is deflected along a path of the human body, and is provided as a support that supports the wire 120. The shape of the flexible backbone 110 may be various. For example, the shape of the flexible backbone 110 may be a tubular shape having a circular cross-section. Then, a hollow may be famed in the interior of the tube, but the hollow may not be formed.

One end of the flexible backbone 110 may be connected to the handler 140, which is not introduced into the human body, and an opposite end of the flexible backbone 11 may be connected to the end effector 150, which is introduced into the human body.

The wire 120 may be provided in a spiral shape which is wound on the outer circumferential surface of the flexible backbone 110 in a multiple of 360 degrees, and the multiple is a positive integer of 1 or more. Then, the multiple in the expression of the multiple of 360 degrees means substantially a multiple of 360 degrees, and may be understood as a concept including an error range.

The wire 120 may deliver the operation force provided by the handler 140 to the end effector 150. The wire 120, for example, may be made of iron. Two or more wires 120 may be provided. Hereinafter, for convenience of description, it is assumed that the wires 120 include first to third wires W1, W2, and W3.

The wire protection part 130 provides a movement path of the wire 120. The wire protection part 130 is provided in a spiral shape which is wound on the outer circumferential surface of the flexible backbone 110 like the wire 120, and two or more wire protection parts 130 may be provided. The wire protection part 130 may have a tubular shape having a hollow in the interior thereof. The hollow of the wire protection part 130 may provide a movement path along which the wire 120 may move. The inner diameter of the wire protection part 130 may be larger than the outer diameter of the wire 120. Accordingly, the wire 120 may have a marginal space in the widthwise direction of the wire 120.

To achieve this, as illustrated in FIG. 4, the wire protection part 130 may include a first wire protection part 130a for the first wire W1, a second wire protection part 130b for the second wire W2, and a third wire protection part 130c for the third wire W3.

According to an embodiment, the wire protection part 130 may be formed of rubber, a synthetic resin, or plastic, which has a low reactivity with a tissue of a human body.

The wire protection part 130 may be provided to be fixed to the flexible backbone 110. For example, the wire protection part 130 may be provided to be bonded to the outer circumferential surface of the flexible backbone 110. Further, when the wire protection part 130 defines a spiral shape on the outer circumferential surface of the flexible backbone 110, an adjacent side surface of the wire protection part 130 may be provided to be bonded. In more detail, the side surfaces of the first wire protection part 130a, the second wire protection part 130b, and the third wire protection part 130c may be provided to be bonded to each other.

Because the wire protection part 130 is bonded and fixed to the outer circumferential surface of the flexible backbone 110, the wire 120 provided in the hollow in the interior of the wire protection part 130 may be provided to be fixed to a predetermined location of the outer circumferential surface of the flexible backbone 110. In other words, even when the flexible backbone 110 is deflected, the wire 120 may be located on the outer circumferential surface of the flexible backbone 110 in the same way before the flexible backbone 110 is deflected. If the flexible backbone 110 is deflected when the wire protection part 130 is not provided to be bonded to the outer circumferential surface of the flexible backbone 110, the spiral shape defined on the outer circumferential surface of the flexible backbone 110 by the wire protection part 130 may change inconstantly. For example, the interval between the side surfaces of the wire protection parts 130 may become smaller on the inside of the deflection with reference to the deflection direction of the flexible backbone 110, and may become larger on the outside of the deflection. Accordingly, when the flexible backbone 110 is deflected, the spiral shape of the wire protection part 130 is not wound or released constantly, and accordingly, the wire 120 provided in the wire protection part 130 may be influenced.

According to an embodiment, after the wire 120 is introduced into the interior of the wire protection part 130, the wire protection part 130 may be fixed to the flexible backbone 110. According to another embodiment, after the wire protection part 130 is fixed to the flexible backbone 110, the wire 120 may be introduced into the wire protection part 130.

Further, according to an embodiment, the wire protection parts 130 may be fixed to the flexible backbone 110 one by one, or may be fixed to the flexible backbone 110 at once. In detail, after the first wire protection part 130a is fixed to the flexible backbone 110, the second and third wire protection parts 130b and 130c may be sequentially fixed to the flexible backbone 110. Further, the first to third wire protection parts 130a, 130b, and 130c may be fixed to the flexible backbone 110 at once.

The handler 140 may include an operation part 142 and a wire driving part 144. If the medical operator drives the wire driving part 144 by operating the operation part 142, an operation force may be provided to the wire 120 and may be delivered to the end effector 150. For example, the operation part 142 may be provided in the form of a handle.

The end effector 150 may directly connect a target portion, and may perform a specific action according to the operation force provided by the handler 140. For example, the end effector 150 may be provided in various forms, such as a nipper, a knife, a camera, or a gripper, according to the purpose of use.

Figure 5:
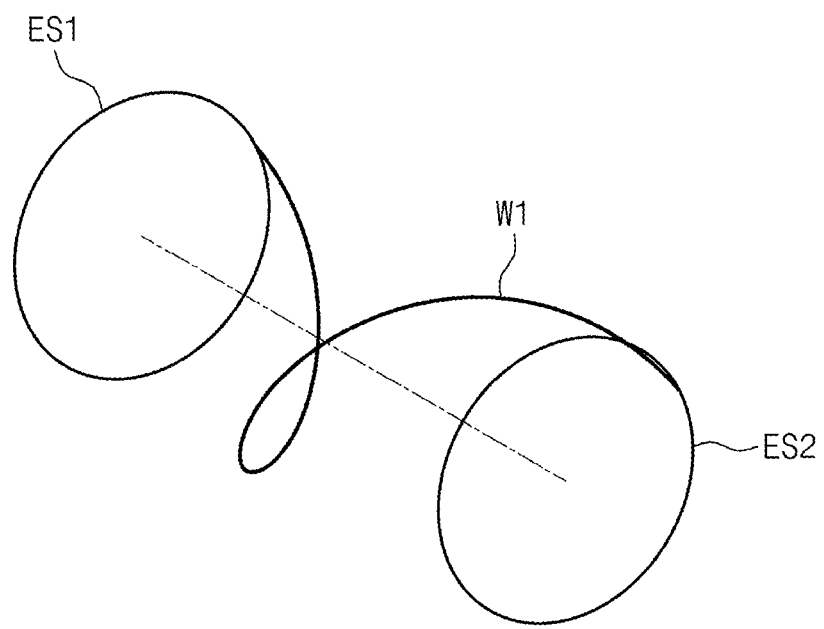
FIG. 5 is a conceptual view of the flexible mechanism according to the embodiment of the present invention.

FIG. 5 is a conceptual view of the flexible mechanism according to the embodiment of the present invention. In more detail, mainly the first wire W1 of the flexible mechanism illustrated in FIG. 4 will be described with reference to FIG. 5. Further, the wire protection part will be omitted in the description.

Referring to FIG. 5, the flexible mechanism has a structure in which the first wire W1 is wounded on the outer circumferential surface of the flexible backbone, and may be wound on the first cross-section ES1 to the second cross-section ES2 of the flexible backbone in a multiple of 360 degrees. In another aspect, the flexible backbone may function as a support such that the first wire W1 has a spiral shape.

Because the first wire W1 is wound on the first cross-section ES1 to the second cross-section ES2 of the flexible backbone in a multiple of 360 degrees, it may be understood that the first wire W1 may has a spiral shape.

Then, the multiple of 360 degrees, by which the first wire W1 is wound on the first cross-section ES1 to the second cross-section ES2 of the flexible backbone, may be various according to the length of the flexible backbone.

Meanwhile, although mainly the first wire W1 has been described with reference to FIG. 5, it is apparent that the technical spirit may be applied to other wires.

Figure 6A:
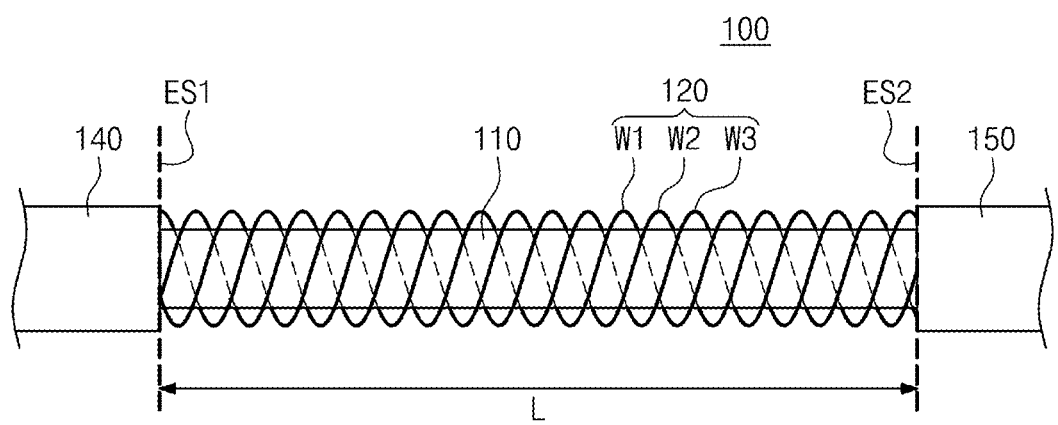
FIGS. 6A and 6B are views of the flexible mechanism according to the embodiment of the present invention.
Figure 6B:
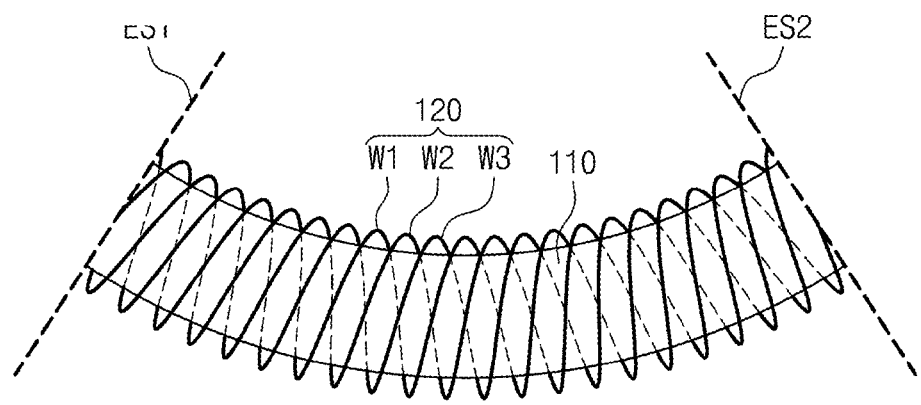

FIGS. 6A and 6B are views of the flexible mechanism according to the embodiment of the present invention.

Referring to FIGS. 6A and 6B, even if the flexible mechanism 100 is deflected, the distances between the first cross-section ES1 and the second cross-sections ES2 of the wires W1, W2, and W3 may be the same as those of the initial state before the flexible mechanism 100 is deflected.

In detail, referring to FIG. 6A again, when the flexible backbone 110 has a linear form, a distance between a first cross-section ES1 and a second cross-section ES2 of the flexible backbone 110 may be L. In this case, distances between the first cross-sections ES1 and the second cross-sections ES2 of the wires W1, W2, and W3 provided in the interior of the flexible backbone 110 may be L'. L' may be larger than L, and it is understood that this is because the wire is wound on the outer circumferential surface of the flexible backbone.

As illustrated in FIG. 6B, when the flexible mechanism 100 is deflected, the distance between the first cross-section ES1 and the second cross-section ES2 of the flexible backbone 110 may become longer or shorter than that of initial state L. That is, the inner side of the deflection may become shorter than L of the initial state, and the outer side of the deflection may be longer that L of the initial state. However, even in this case, the distances between the cross-sections ES1 and the second cross-sections ES2 of the wires W1, W2, and W3 may be maintained constantly. In other words, the first wire W1 does not protrude to the outside of the first cross-section ES1 and the second cross-section ES2. Further, the third wire W3 is not introduced into the first cross-section ES1 and the second cross-section ES2. Accordingly, the operation force of the handler 140 is precisely delivered to the end effector 150, and thus, the precision of a medical operation and/or a surgery using the flexible mechanism 100 can be enhanced. Hereinafter, a mechanism of constantly maintaining the length of a wire even when a deflection occurs will be described.

According to an embodiment of the present invention, as described above, a structure in which the wires W1, W2, and W3 are wound on the flexible backbone 110 in a spiral shape is provided. Accordingly, even when the flexible mechanism 100 is deflected, the lengths of the paths of the wires W1, W2, and W3 can be constantly maintained. That is, regardless of whether the posture of the flexible backbone 110 is in a linear state or is deflected, the length of the wire between opposite ends of the flexible backbone can be constantly maintained. In detail, if the flexible backbone 110 is deflected, the length of the inner area of the flexible backbone 110 becomes shorter than L of the initial state and the length of the outer area of the flexible backbone 110 becomes larger than L of the initial state. Then, because the wires W1, W2, and W3 are wound on the flexible backbone 110 in a spiral shape, they are influenced by all of the length changes occurring in the inner area and the outer area of the flexible backbone 110. In other words, the wire part located in the inner area becomes loose, and the wire part located in the outer area becomes tight. Accordingly, the loosened area of the wire and the tightened area of the wire are offset. Accordingly, even when the flexible mechanism 100 is deflected, the lengths of the wires W1, W2, and W3 between one end ES1 and an opposite end ES2 of the flexible backbone 110 can be maintained constantly. In order to obtain the effect, the period at which the wires are wound on the flexible backbone has to be a multiple of 360 degrees.

An experimental description of the effect of the present invention will be described below with reference to FIGS. 9A and 9B.

Figure 7:
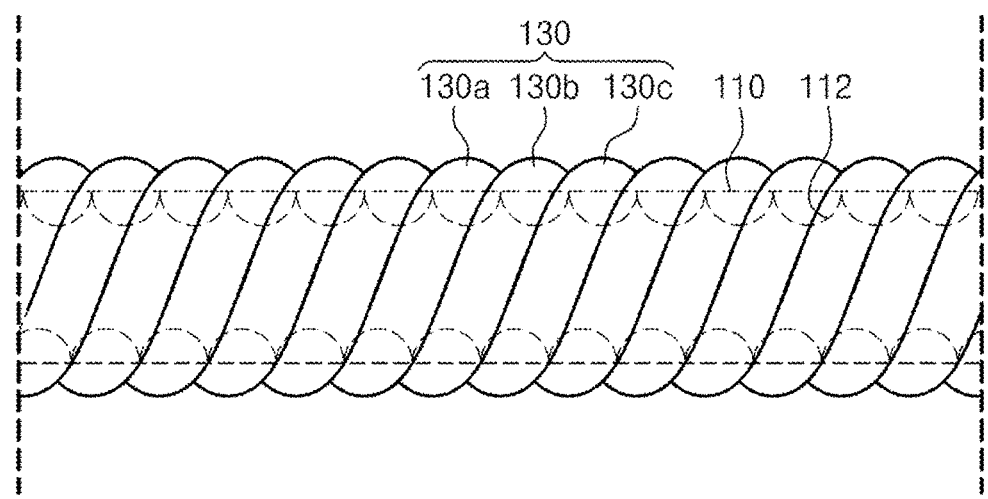
FIG. 7 is a view of the flexible mechanism according to a modification of the present invention.

FIG. 7 is a view of the flexible mechanism according to a modification of the present invention.

Although it is assumed in the embodiment described with reference to FIG. 5 that the surface of the flexible backbone 110 is planar, the modification which will be described with reference to FIG. 7 has a difference in that a groove 112 is formed on the surface of the flexible backbone 110.

Referring to FIG. 7, the groove 112 may be formed on the outer circumferential surface of the flexible backbone 110. The groove 112 is formed in a form corresponding to the form of the wire protection part 130. Accordingly, when the wire protection part 130 is wound on the flexible backbone 110, it may be adhered and fixed to the flexible backbone 110.

The groove 112 may be formed through a method of applying a pressure to the surface of the flexible backbone 110 or a method of etching the surface of the flexible backbone 110.

Figure 8:
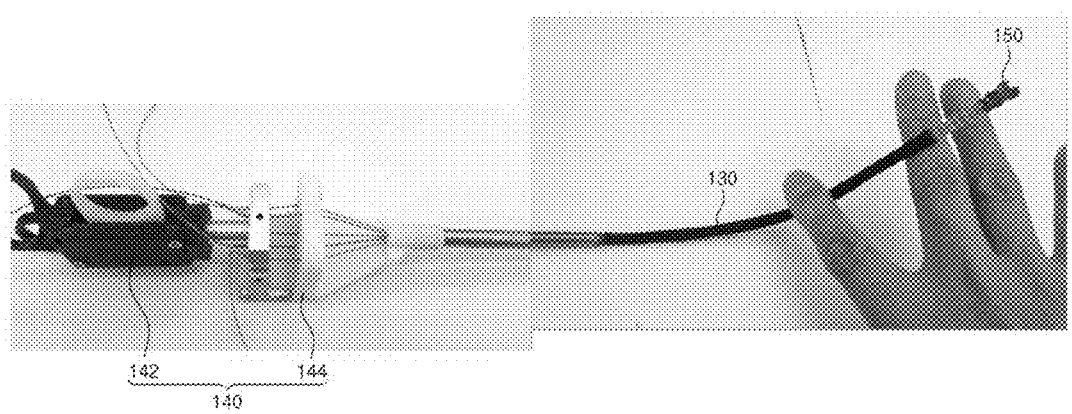
FIG. 8 is a view of the flexible mechanism manufactured according to the embodiment of the present invention.

FIG. 8 is a view of the flexible mechanism manufactured according to the embodiment of the present invention. FIGS. 9A and 9B are views illustrating an experimental example of the flexible mechanism of FIG. 8.

Referring to FIG. 8, the flexible mechanism may include a handler 140 including an operation part 142 and a wire driving part 144, a wire protection part 130 including a wire, and an end effector 150. A structure in which the wire protection part 130 is wound on the flexible backbone in a multiple of 360 degrees in a spiral form may be provided.

Figure 9A:
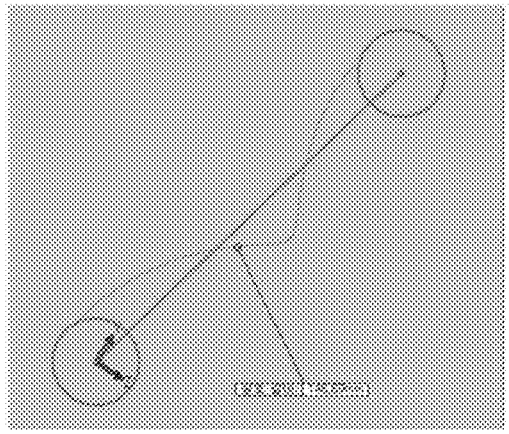
FIGS. 9A and 9B are views illustrating an experimental example of the flexible mechanism of FIG. 8.
Figure 9B:
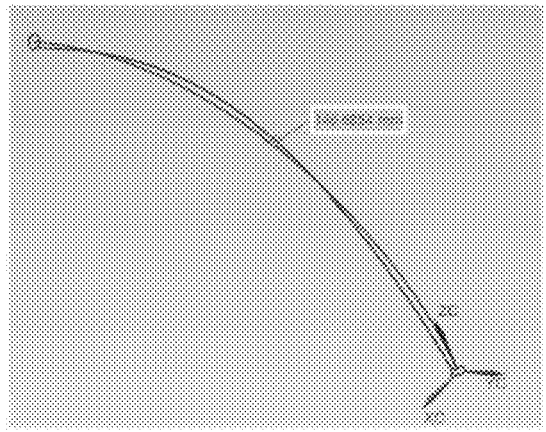

FIG. 9A illustrates a flexible mechanism that is not deflected. Referring to FIG. 9A, it can be seen that one wire is wound by 360 degrees along the outer circumferential surface of the flexible backbone between opposite cross-sections of the flexible backbone. Then, the length of the path of the wire is measured to be 146.69 mm. FIG. 9A illustrates a flexible mechanism that is deflected. Even when the flexible backbone is deflected, the length of the wire between the opposite ends of the flexible backbone is 146.6854 mm and it can be seen that the result is substantially not different from the case in which the flexible backbone is in a linear form. In other words, it can be seen that the relative displacement between an end of the flexible backbone and an end of the wire is constantly maintained. That is, it can be seen that a phenomenon in which the wire is operated to the outside or inside of the flexible backbone unintentionally even when the flexible mechanism is deflected can be prevented.

According to the present invention, an unintended operation by a deflection when the flexible mechanism is inserted into a human body having many curves can be basically prevented. As described with reference to FIGS. 1 and 2, the general flexible mechanism undergoes a phenomenon in which a wire is unintentionally pulled or released with respect to the end effector due to a deflection. This causes a severe disadvantage because it causes a difficulty in operating the wire, causes breaking of the wire, and causes an unintended operation of the end effector.

However, according to an embodiment of the present invention, because the wire is wound on the flexible backbone in a multiple of 360 degrees, the wire is neither pulled nor released with respect to the end effector even when a deflection occurs. That is, a phenomenon in which the wire is relatively displaced to the outside or inside of the flexible backbone due to the deflection can be eliminated. Accordingly, the embodiment of the present invention can perform a steering operation of an existing endoscope more smooth and can increase the life span of the endoscope. Further, it is apparent that the embodiment of the present invention can be applied to a laparoscope surgical tool, and it is also apparent that the embodiment of the present invention can be applied to an industrial endoscope device that diagnoses the interior of a curved pipe line.

Further, although it has been described with an assumption that the wire of the flexible mechanism according to the embodiment of the present invention is provided on the outer circumferential surface of the flexible backbone, the wire may be provided on the inner circumferential surface of the flexible backbone. Then, the feature that the wire is provided on the inner circumferential surface of the flexible backbone may mean that the passage for the spiral wire may be formed on the surface of the flexible backbone and may be formed on the inner side of the flexible backbone.

In detail, the flexible backbone further includes a spiral wire passage that is recessed from the surface of the flexible backbone, and the wire may pass from one end to an opposite end of the flexible backbone along the spiral wire passage in a multiple of 360 degrees. In other words, a spiral wire passage that passes the spiral passage formed in the interior of the cross-section of the flexible backbone from one end to an opposite end of the flexible backbone in a multiple of 360 degrees may be formed, and accordingly, the wire may pass through the spiral wire passage in a multiple of 360 degrees.

Meanwhile, the backbone according to the embodiment of the present invention has flexible characteristics while going to a medical operation part in a human body, but may have rigid characteristics in a step of a medical operation after arriving at the medical operation part (flexible to rigid). This is for eliminating the inaccuracy of the medical operation due to shaking of the backbone in the medical operation step.

Although the preferred embodiments of the present invention have been described in detail until now, the scope of the present invention is not limited to the embodiments and should be construed by the attached claims. Further, it should be understood that those skilled in the art to which the present invention pertains may variously correct and modify the present invention without departing from the scope of the present invention.

What is claimed is:

1. A flexible mechanism comprising:
  a single flexible backbone introduced into a medical operation part in a human body and deflected along a path in the human body; and
  at least two wires configured to deliver an operation force provided through a handler provided at one end of the single flexible backbone to an end effector provided on an opposite end of the single flexible backbone,
  wherein the at least two wires extend from the one end to the opposite end of the single flexible backbone, and are wound on an outer circumferential surface of the single flexible backbone by a multiple of 360 degrees,
  wherein at least two wire protection parts are wound on the outer circumferential surface of the single flexible backbone from the one end to the opposite end of the single flexible backbone by a multiple of 360 degrees and provide at least two movement paths for the wires,
  wherein at least two grooves wound on the outer circumferential surface of the single flexible backbone from the one end to the opposite end of the single flexible backbone by a multiple of 360 degrees are formed on the outer circumferential surface of the single flexible backbone, and
  wherein the at least two wire protection parts are seated in the at least two grooves,
  wherein the at least two wire protection parts are bonded to the outer circumferential surface of the single flexible backbone such that the at least two wire protection parts are wound around the single flexible backbone in a spiral shape, and
  wherein adjacent side surfaces of the at least two wire protection parts are bonded such that the entirety of the outer circumferential surface of the single flexible backbone is covered by the at least two wire protection parts.

2. The flexible mechanism of claim 1, wherein the length of areas of the at least two wires, which protrude to opposite ends of the single flexible backbone, is constant even when the single flexible backbone is deflected.

3. The flexible mechanism of claim 1, wherein the at least two wires are wound on the outer circumferential surface of the single flexible backbone by a multiple of 360 degrees in a spiral shape.

4. The flexible mechanism of claim 1, wherein the multiple is a positive integer of 1 or more.

5. The flexible mechanism of claim 1, wherein the at least two wires are respectively provided along the at least two movement paths of the at least two wire protection parts.

\* \* \* \* \*